(12) United States Patent
Jackson et al.

(10) Patent No.: US 6,437,152 B1
(45) Date of Patent: Aug. 20, 2002

(54) INTERMEDIATE FOR THE SYNTHESIS OF PROSTAGLANDINS

(75) Inventors: Philip Mark Jackson; Ian Campbell Lennon, both of Cambridge (GB)

(73) Assignee: Chirotech Technology, Inc. (GB)

( * ) Notice: Subject to any disclaimer, the term of this patent is extended or adjusted under 35 U.S.C. 154(b) by 0 days.

(21) Appl. No.: 09/898,241

(22) Filed: Jul. 3, 2001

Related U.S. Application Data

(62) Division of application No. 09/547,205, filed on Apr. 12, 2000, now Pat. No. 6,294,679
(60) Provisional application No. 60/136,464, filed on May 28, 1999.

(30) Foreign Application Priority Data

Apr. 12, 1999 (GB) ............................................. 9908326

(51) Int. Cl.$^7$ ...................... C07D 313/06; C07D 507/02
(52) U.S. Cl. ...................... 549/355; 549/354; 549/214; 549/263
(58) Field of Search ................................ 549/214, 354, 549/355

(56) References Cited

U.S. PATENT DOCUMENTS 4,409,213 A * 10/1983 Collington et al. ......... 424/244
4,824,993 A    4/1989 Collington et al.

FOREIGN PATENT DOCUMENTS

EP          0074856         9/1982
EP          0639563     *   2/1995

OTHER PUBLICATIONS

Lee, Thomas V., Stanley M. Roberts, Michael J. Dimsdale, Roger F. Newton, D. Kenneth Rainey, Colin F. Webb (1978) *J. Chem. Soc.*, Perkin Trans. 1:1176–1179.
Corey and Cheng, The Logic of Chemical Synthesis, Wiley, 1989, p. 250–266.
Newton et al. (1980) *Tetrahedron* 36:2163–2196.

* cited by examiner

*Primary Examiner*—Alan L. Rotman
*Assistant Examiner*—Rita Desai
(74) *Attorney, Agent, or Firm*—Saliwanchik, Lloyd & Saliwanchik

(57) ABSTRACT

An enantiomerically enriched compound of formula 1,

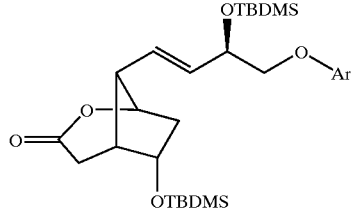

(1)

wherein Ar is phenyl optionally substituted with one or more groups selected from haloalkyl, alkyl and halide. This compound can be isolated in crystalline form, and used in the preparation of (+)-16-[3-trifluoromethyl)phenoxy]-17,18,19,20-tetranor $PGF_{2\alpha}$ isopropyl ester.

3 Claims, No Drawings

INTERMEDIATE FOR THE SYNTHESIS OF PROSTAGLANDINS

CROSS-REFERENCE TO A RELATED APPLICATION

This application is a divisional application of U.S. Ser. No. 09/547,205, filed Apr. 12, 2000, now U.S. Pat. No. 6,294,679. This application also claims the benefit of U.S. provisional application Ser, No. 60/136,464, filed May 28, 1999.

FIELD OF THE INVENTION

This invention relates to the preparation of a novel crystalline lactone and its use in prostaglandin synthesis.

BACKGROUND OF THE INVENTION

The synthetic prostaglandin 16-[3-(trifluoromethyl)phenoxy]-17,18,19,20-tetranor $PGF_{2\alpha}$ and its ester derivatives, in particular the isopropyl ester (2), are potent drugs for the treatment of glaucoma and ocular hypertension. Optimum therapeutic benefit is achieved when compound (2) is used in the form of the dextrorotatory single enantiomer (+)-2, as depicted below. For development as a pharmaceutical product, an economically viable route is required for the synthesis of (+)-2 in quantities of at least 1 kg.

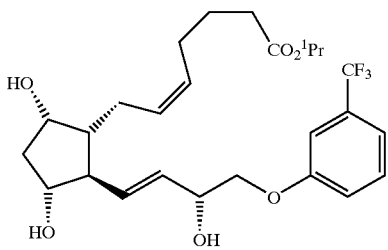

(2)

EP-A-0639563 describes biological studies of compound 2 and analogues, and synthetic methods which are applicable to its preparation. The synthetic strategy employed is based on that used by Corey in his pioneering synthesis of prostaglandin $F_{2\alpha}$ (Corey and Cheng, The Logic of Chemical Synthesis, Wiley, 1989, p. 250–266 and references therein), wherein the cyclopentane ring embedded in a lactone intermediate of type 3 (PG=protecting group, e.g. Me) has relative stereochemistry correctly defined across four chiral centres. Lactones of type 3 can be prepared in single enantiomer form. Although such a route was successfully utilised to prepare small quantities of (+)-2 for preliminary biological evaluation, for a number of reasons it is unsuitable for industrial manufacture as a high-purity pharmaceutical product for administration to human patients. At least 15 steps (from cyclopentadiene) are required, with loss of yield in individual steps exacerbated by the linear nature of the synthesis. Fractional column chromatography is required after many of these steps to effect purification of intermediates. For example, a late stage stereoselective reduction of a 15-keto function in the ω-side chain using (−)-B-chlorodiisopinocampheylborane requires the removal of the unwanted 15S isomer, formed as a by-product, by a chromatographic separation.

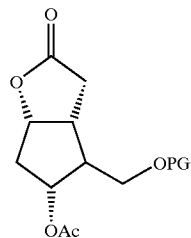

(3)

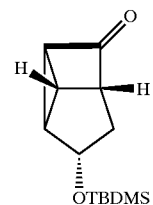

(4)

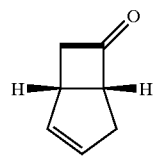

(5)

An alternative and more convergent approach to prostaglandins involves addition of a cuprate reagent, incorporating the entire ω-side chain, to the tricyclo[3.2.0.0$^{2.7}$]heptanone 4 (Lee et al, J. Chem. Soc., Perkin Trans 1, 1978,1176). Tricyclic ketone 4 is prepared from a TBDMS-protected bromohydrin which is in turn derived from bicyclo[3.2.0]hept-2-en-6-one (5). In comparison to routes proceeding by a Corey lactone of type 3, significantly fewer steps are required. For example, preparation of prostaglandin $F_{2\alpha}$ from compound 5 requires only 8 steps (10 steps from cyclopentadiene). Avoidance of awkward late-stage reduction to establish the required configuration of the C-15-OH functionality provides another advantage.

EP-A-0074856 describes resolution of racemic bicyclo[3.2.0]hept-2-en-6-one (5) by forming diastereomeric salts of its α-hydroxysulfonic acid derivative with a chiral amine, and separation by crystallisation.

Certain lactones are described in Newton et al, Tetrahedron, 1980, 2163. None is crystalline.

SUMMARY OF THE INVENTION

This invention is based on the unexpected discovery of a crystalline lactone 1

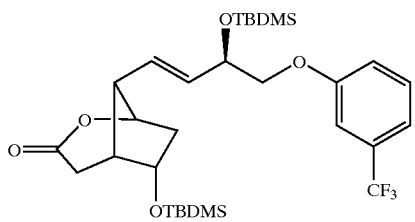

(1)

This compound can be used in the stereoselective synthesis of 16-[3-(trifluoromethyl)phenoxy]-17,18,19,20-tetranor $PGF_{2\alpha}$ and its ester derivatives, for example (+)-2. The crystalline lactone can be obtained in highly pure form. The crystallinity of the lactone is crucial in enabling impurities to be removed at this stage without resort to column chromatography. This provides the basis for an industrially viable synthesis of the prostaglandin 2 for pharmaceutical use.

According to the invention, this discovery may also be applied to other substituted 16-phenoxy prostaglandins, where the substituent is haloalkyl, alkyl or halide. The alkyl group may have up to 6 C atoms. Halide is preferably 3-Cl.

DESCRIPTION OF THE INVENTION

By way of illustration, the synthesis of the lactone 1 is depicted in Scheme I. All reactants depicted are used in enantiomerically enriched form, typically in >95% ee or higher.

Step (i) is the preparation of the tricyclic ketone 4. This is achieved by treatment of the bromohydrin 6 with base in an appropriate solvent, preferably potassium tert-butoxide in toluene. The unstable tricycle 4 is used without purification in step (iii). It is not necessary to evaporate the tricycle solution to dryness.

Step (ii) is the formation of an alkenylcuprate reagent from the vinyl iodide 7, precursor to the ω-side chain. The preparation of vinyl iokide 7 in enantiomerically enriched form is disclosed in U.S. Pat. No. 6,214,611, issued Apr. 10, 2001, entitled Process for the Preparation of Prostaglandin precursors, and claiming priority from British Patent Application No. 9908327.1. The vinyl iodide is metallated with an alkyllithium reagent, preferably tert-butyllithium, and then treated with a cuprate of the form RCu(CN)Li where R is a non-transferable group which may be 2-thienyl. Step (iii) is reaction of the alkenylcuprate with the tricycle to form the bicyclic ketone 8.

Step (iv) is the Baeyer-Villiger reaction producing the lactone 1. A peracid, preferably peracetic acid, is used, resulting in a 3:1 mixture of regioisomers, isolated as an oil. Further processing is then required to render this material as usable in subsequent steps. Conveniently, the minor and unwanted regioisomer can be selectively hydrolysed by treatment with aqueous alkali, for example, aqueous sodium hydroxide in acetonitrile. Extraction of the unreacted lactone 1 into an organic solvent, followed by evaporation of solvent, yields a solid residue which can be recrystallised at low temperature to give highly pure crystalline material with convenient handling and storage characteristics. These processing operations are pivotal to the success of the overall synthetic route.

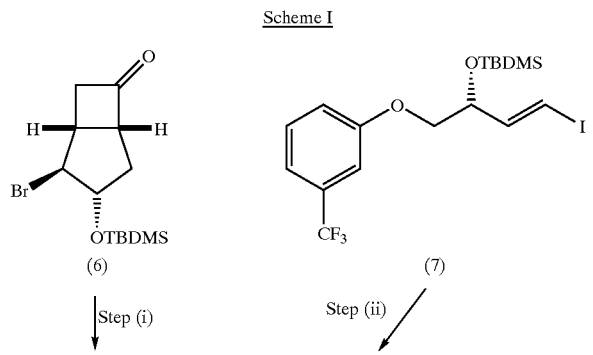

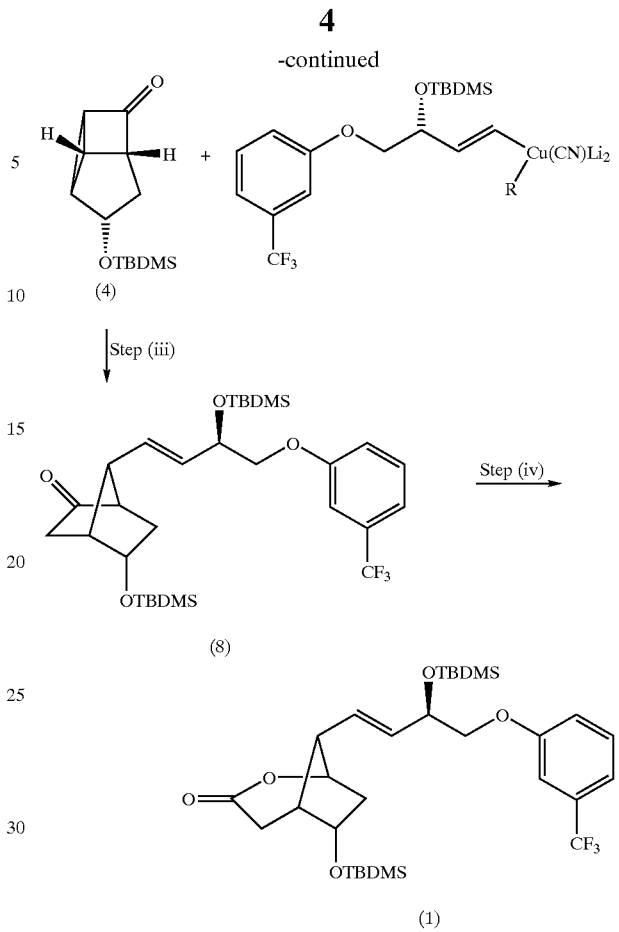

Scheme II summarises the conversion of lactone 1 to the target prostaglandin (+)-2, using conventional processes (for analogous methods see Lee et al, *J. Chem. Soc., Perkin Trans* 1, 1978,1176; and EP-A-0639563). Typically, reduction to the lactol using diisobutylaluminium hydride is followed by Wittig reaction with the ylide generated from (4-carboxybutyl)triphenylphosphonium bromide and potassium tert-butoxide. Esterification and O-deprotection steps complete the synthesis.

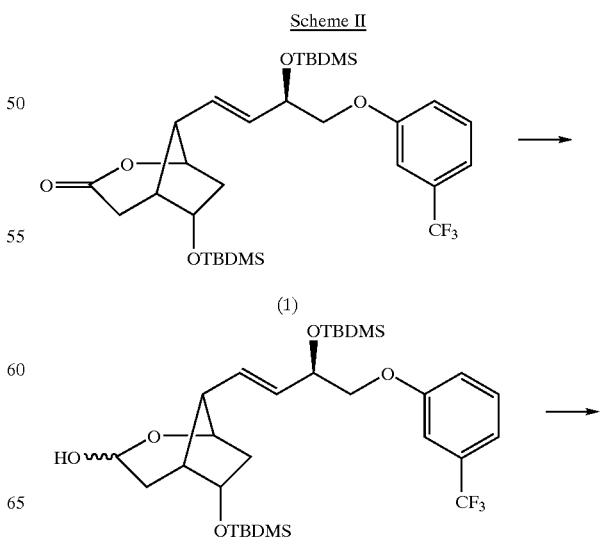

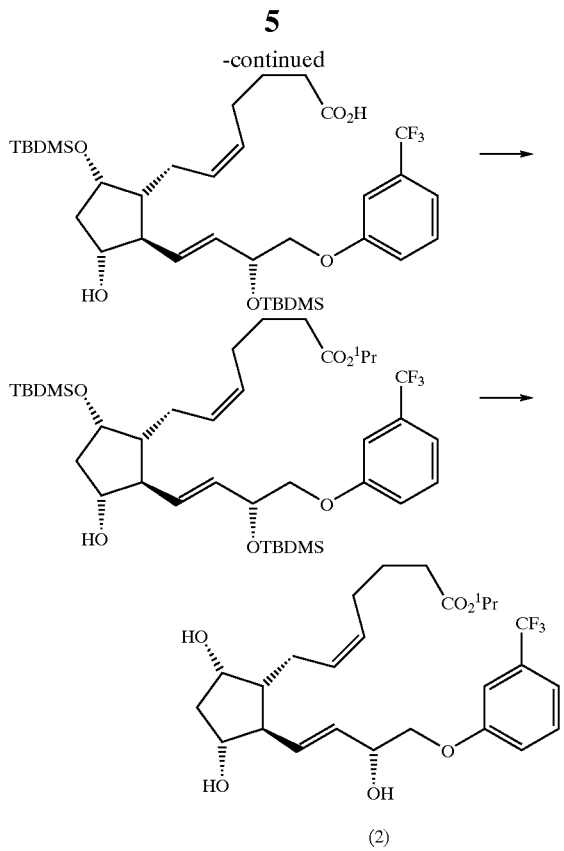

(2)

The following Examples illustrate the invention.

EXAMPLE 1

3-Endo-tert-Butyldimethylsilyloxytricyclo[3.2.0.0$^{2.7}$]heptan-6-one

Potassium tert-butoxide (114.2 g, 1.02 mol) is suspended in toluene (2 L) and cooled to −15° C. The suspension is stirred under a nitrogen atmosphere and absolution of the bromoketone (250 g, 0.783 mol) in dry toluene (400 ml) is added over 1 hour. The internal temperature is maintained at −10 to −20° C. The mixture is stirred for 1 hour. The mixture is warmed to room temperature, activated carbon (75 g) is added, and the mixture is stirred for 5 minutes. The mixture is filtered through Celite and the cake is washed with toluene (2.5 L). The filtrates are concentrated under reduced pressure, at 20° C., to approximately 700 ml volume. This solution is used directly in the next step.

EXAMPLE 2

7-Anti{4-[3-(Trifluoromethyl)phenoxy]-3(R)-tert-butyldimethylsilyloxy-1(E)-butenyl}-5-endo-tert-butyldimethylsilyloxybicyclo[2.2.1]hepten-2-one A dry 10 L flange flask, fitted with an overhead stirrer, temperature probe, nitrogen inlet and pressure equalised dropping funnel, is purged with nitrogen and cooled to −70° C. A solution of tert-butyllithium (1.7 M in pentane, 1013 ml, 1.72 mol) is added. The solution is re-cooled to −70° C. and a solution of the vinyl iodide (436 g, 0.923 mol) in diethyl ether (1.3 L) is added over 90 minutes, maintaining the internal temperature below −60° C.

In the mean time, thiophene (75.2 ml, 0.94 mol) is placed in a dry 2 L 3-necked flask, under a nitrogen atmosphere. THF (600 ml) is added, and the solution is cooled to −30° C. n-Butyllithium (2.5 M in hexanes, 376 ml, 0.94 mol) is added over 20 minutes. The solution is stirred for 20 minutes at −20° C., then the resulting yellow solution is added to a suspension of copper(I) cyanide (84.15 g, 0.94 mol) in THF (800 ml) at −20° C. over 15 minutes. The resulting dark brown solution is re-cooled to −10° C., and stirred for 20 minutes.

The freshly prepared lithium 2-thienylcyanocuprate solution, at −10° C., is added to the vinyllithium solution at −70° C. over 20–30 minutes. The resulting solution is stirred for 30 minutes at −70° C. The tricycle solution (approximately 187 g in 600 ml toluene, +100 ml THF added) is cooled to −70° C., and added to the cuprate solution, at −70° C. over 20 minutes. The mixture is stirred at −70° C. for one hour, then the cooling bath is removed from the reaction vessel and saturated ammonium chloride (3 L) is added. The mixture is stirred for 20 minutes, the aqueous layer becomes deep blue in colour and a yellow/green precipitate forms. The mixture is filtered through a No 3 filter paper and the filter cake is washed with methyl tert-butyl ether (1 L). The organic layer is separated, and the aqueous layer is extracted with methyl tert-butyl ether (1 L). The combined organic layers are washed with brine (2 L), dried (MgSO$_4$) and decolourised with activated carbon. After 20 minutes the solution is filtered, the cake is washed with methyl tert-butyl ether (2.5 L), and the filtrate is evaporated under reduced pressure.

The residue is taken up in heptane and passed through a plug of silica (1.5 Kg), eluting with 2% EtOAc/heptane to 10% EtOAc/heptane to provide the pure ketone as a yellow solid (293 g, 64%), m.p. 64–72° C.; $[\alpha]_D^{20}$+35.9° (c=1.05, DCM); $\delta_H$(400 MHz, CDCl$_3$) 7.38 (1H, t, J 8), 7.25 (1H, d, J 8), 7.13 (1H, s), 7.07 (1H, d, J 8), 5.86 (1H, dd, J 16, 8), 5.73 (1H, dd, J 16, 6), 4.55 (2H, m), 3.90 (2H, d, J 7), 2.80 (1H, m), 2.77 (1H, d, J 18), 2.57 (2H, m), 2.45 (1H, m), 2.05 (1H, dd, J 18, 4), 1.35 (1H, m), 0.95 (9H, s), 0.90 (9H, s), 0.15 (3H, s), 0.14 (3H, s) and 0.05 (6H, s); $\delta_C$ (100 MHz, CDCl$_3$) 216.0, 158.82, 132.02, 131.54 (q, J 32), 129.98, 127.77, 123.90 (q, J 270), 118.04, 117.55, 111.13, 72.32, 71.34, 69.92, 54.37, 50.23, 46.24, 38.80, 33.39, 25.76, 18.30, 17.97, −4.67, −4.74, −4.86 and −4.92.

EXAMPLE 3

8-Anti{4-[3-(trifluoromethyl)phenoxy]-3(R)-tert-butyl-dimethylsilyl-1(E)-butenyl}-6-endo-tert-butyldimethylsilyloxy-2-oxabicyclo[3.2.1]octan-3-one The ketone (362.6 g, 0.62 mol) and sodium acetate (170 g, 2.07 mol) are dissolved in glacial acetic acid (1.7 L). The reaction vessel is placed in a water bath at 20° C. and peracetic acid (40% in dilute acetic acid, 176.7 ml, 0.93 mol) is added over a period of 20 minutes. The solution is stirred at room temperature for 3 h. More peracetic acid (30 ml) is added, and the solution is stirred for a further 2 h. The reaction mixture is poured onto water (2.5 L), and the products are extracted into MTBE (2×750 ml, then 500 ml). The combined organic phases are washed with water (2 L). The aqueous phase is back extracted with MTBE (500 ml). The combined organic extracts are neutralised with saturated sodium carbonate solution (500 ml) and water (2 L) is added to aid phase separation. The organic phase is washed with water (1 L), brine (1 L), dried (MgSO$_4$) and evaporated under reduced pressure, to give a yellow oil (363.8 g). The crude product (consisting of a mixture of regioisomers) is dissolved in acetonitrile (1 L) at room temperature. Sodium hydroxide solution (1M, 300 ml) is added and the solution stirred at room temperature for 2 h. Water (1 L) is added and the product is extracted into MTBE (3×500 ml). The combined organic phases are washed with brine (500 ml), dried (MgSO$_4$), filtered and evaporated under reduced pressure. The residue is recrystallised from heptane (1 L) at −70° C. (cold bath temperature), filtered and washed with cold (−70° C., cold bath) heptane (2×200 ml). The solid is dried, to give the lactone as a white solid (141.2 g, 38%). The mother liquors are filtered through silica gel (1 Kg) eluting with 20% DCM/Heptane, to remove baseline. Recrystallisation from cold (−70° C., cold bath) heptane (400 ml) gave a second batch of lactone (34 g, 9%), m.p. 77–78° C.; $[\alpha]_D^{20}$−10.9° (c=1.05, DCM); $\delta_H$ (400 MHz, CDCl$_3$) 7.40 (1H, d, J 8), 7.22 (1H, d, J 8), 7.10 (1H, s), 7.05 (1H, d, J 8), 5.70 (2H, m), 4.52 (3H, m), 3.87 (2H, d, J 6), 3.16 (1H, d, J 18), 3.00 (1H, d, J 6), 2.56 (1H⁻, dd, J 18, 6), 2.46 (1H, m), 2.39 (1H, m), 1.88 (1H, dt, J 16, 3), 0.95 (9H, s), 0.89 (9H, s), 0.10 (6H, s) and 0.04 (6H, s); $\delta_C$ (100 MHz, CDCl$_3$) 170.39, 158.75, 132.43, 131.92 (q, J 32), 130.05, 127.87, 123.91 (q, J 270), 118.06, 117.68, 111.11, 82.20, 72.26, 71.64, 71.10, 48.94, 42.48, 40.40, 33.05, 25.75, 18.30, 18.04, −4.64, −4.76, −4.88 and −5.10.

The lactone of example 7 can be converted to (+)-16-[3-(trifluoromethyl)phenoxy]-17,18,19,20-tetranor PGF$_{2\alpha}$ isopropyl ester using conventional processes; see Scheme II and associated publications.

We claim:

1. A process for preparing a prostaglandin, or an ester derivative thereof, wherein said process comprises the conversion of a lactone compound of formula 1

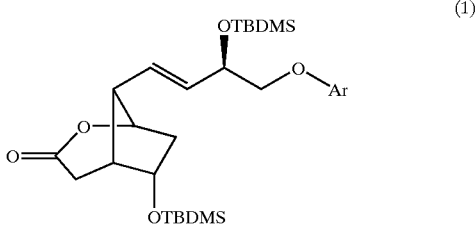

(1)

wherein Ar is phenyl optionally substituted with one or more groups selected from haloalkyl, alkyl and halide; and wherein said conversion to said prostaglandin comprises the following steps:
   (i) reduction of the lactone to the corresponding lactol,
   (ii) introduction of a prostaglandin α-chain by a Wittig reaction, and
   (iii) conversion of the OTBDMS groups to OH groups.

2. The process according to claim 1, wherein the prostaglandin is (+)-16-[3-trifluoromethyl)phenoxy]-17,18,19, 20-tetranor PGF$_{2\alpha}$ isopropyl ester.

3. The process, according to claim 1, wherein said process further comprises an acid-ester conversion either before or after step (iii).

* * * * *